United States Patent
Borthwick et al.

(10) Patent No.: US 8,202,864 B2
(45) Date of Patent: *Jun. 19, 2012

(54) COMPOUNDS

(75) Inventors: Alan David Borthwick, Stevenage (GB); Deirdre Mary Bernadette Hickey, Stevenage (GB); John Liddle, Stevenage (GB); Andrew McMurtrie Mason, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/035,366

(22) Filed: Feb. 25, 2011

(65) Prior Publication Data

US 2011/0152262 A1  Jun. 23, 2011

Related U.S. Application Data

(63) Continuation of application No. 12/850,386, filed on Aug. 4, 2010, now Pat. No. 7,919,492, which is a continuation of application No. 12/480,182, filed on Jun. 8, 2009, now abandoned, which is a continuation of application No. 11/630,179, filed as application No. PCT/EP2005/006760 on Jun. 21, 2005, now Pat. No. 7,550,462.

(30) Foreign Application Priority Data

Jun. 23, 2004 (GB) .................................. 0414093.5

(51) Int. Cl.
*A61K 31/5377* (2006.01)
*C07D 413/14* (2006.01)

(52) U.S. Cl. ...................................... 514/235.8; 544/121

(58) Field of Classification Search ........................ None
See application file for complete search history.

(56) References Cited

U.S. PATENT DOCUMENTS

| | | | |
|---|---|---|---|
| 4,596,819 A | 6/1986 | Nicolaides et al. | |
| 5,464,788 A | 11/1995 | Bock et al. | |
| 5,817,751 A | 10/1998 | Szardenings et al. | |
| 7,550,462 B2 * | 6/2009 | Borthwick et al. | 514/235.8 |
| 7,919,492 B2 * | 4/2011 | Borthwick et al. | 514/235.8 |
| 2005/0148572 A1 | 7/2005 | Borthwick et al. | |
| 2007/0149524 A1 | 6/2007 | Liddle | |
| 2007/0185162 A1 | 8/2007 | Borthwick et al. | |
| 2007/0208031 A1 | 9/2007 | Borthwick et al. | |

FOREIGN PATENT DOCUMENTS

| | | |
|---|---|---|
| DE | 3830096 | 1/2004 |
| GB | 2326639 | 12/1998 |
| WO | 9937304 A1 | 7/1999 |
| WO | 9938844 A1 | 8/1999 |
| WO | 9947549 A1 | 9/1999 |
| WO | 03053443 A1 | 7/2003 |
| WO | 2005000311 A1 | 1/2005 |
| WO | 2005000840 A1 | 1/2005 |
| WO | 2006000400 A1 | 1/2006 |
| WO | 2006000759 A1 | 6/2006 |
| WO | 2006067462 A1 | 6/2006 |

OTHER PUBLICATIONS

Wolff; Burger's Medicinal Chemistry, 5th Ed., Part 1; 1995; pp. 975-977.
Testa et al.; Pure Appl. Chem.; 2004; vol. 76; pp. 907-914.
Akerlund; Prog. Brain. Res.; 2002; vol. 139; pp. 359-365.
Vippagunta et al.; Advanced Drug Delivery Reviews; 2001; vol. 48; pp. 3-26.
Tsatsaris et al.; Drugs; 2004; vol. 64(4) Abstract; pp. 375-382.
Banker et al.; Modern Pharmaceutics, 3rd Ed.; 1996; p. 596.
Grigorash et al.; Chem. Heterocycl. Compound; 1977; vol. 13, No. 12; pp. 1280-1281.
Kolasa et al.; J. Org. Chem.; 1990; vol. 55, No. 6; pp. 1711-1721.
Pettibone et al.; Drug Development Research; 1993; vol. 30, No. 3; pp. 129-142.
Wyatt et al.; Bioorganic & Med. Chem. Letters; 2001; vol. 11, No. 10; pp. 1301-1305.
Stella; "Pro Drugs: An Overview and Definition"; Pro Drugs as Novel Drug Delivery Systems; 1975; Chapter 1; pp. 1-115.

* cited by examiner

*Primary Examiner* — Emily Bernhardt
(74) *Attorney, Agent, or Firm* — Kathryn L. Coulter

(57) ABSTRACT

Compounds of formula (I)

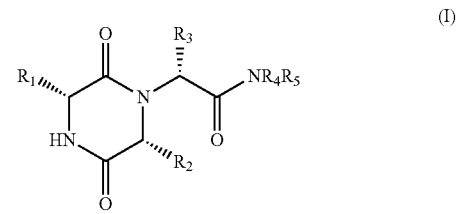

wherein $R_1$ is 2-indanyl, $R_2$ is 1-methylpropyl, $R_3$ is a group selected from 2,6-dimethyl-3-pyridyl or 4,6-dimethyl-3-pyridyl, $R_4$ represents methyl and $R_5$ represents hydrogen or methyl or, $R_4$ and $R_5$ together with the nitrogen atom to which they are attached represent morpholino and pharmaceutically acceptable derivatives thereof are described, as are for their preparation, pharmaceutical compositions containing them and their use in medicine, particularly their use as oxytocin antagonists.

4 Claims, No Drawings

COMPOUNDS

CROSS-REFERENCE TO RELATED APPLICATIONS

This application is a continuation of U.S. application Ser. No. 12/850,386 filed Aug. 4, 2010, now allowed; which is a continuation of U.S. application Ser. No. 12/480,182 filed Jun. 8, 2009, now abandoned; which is a continuation of U.S. application Ser. No. 11/630,179 filed Dec. 19, 2006, issued as U.S. Pat. No. 7,550,462; which was filed pursuant to 35 U.S.C. §371 as a U.S. National Phase Application of International Application No. PCT/EP2005/006760 filed Jun. 21, 2005; which claims priority to Great Britain Application No. 0414093.5, filed Jun. 23, 2004.

FIELD OF THE INVENTION

This invention relates to novel diketopiperazine derivatives having a potent and selective antagonist action at the oxytocin receptor, to processes for their preparation, pharmaceutical compositions containing them and to their use in medicine.

The hormone oxytocin is a potent contractor of the uterus and is used for the induction or augmentation of labour. Also the density of uterine oxytocin receptors increases significantly by >100 fold during pregnancy and peaks in labour (pre-term and term).

Pre-term births/labour (between 24 and 37 weeks) causes about 60% of infant mortality/morbidity and thus a compound which inhibits the uterine actions of oxytocin e.g. oxytocin antagonists, should be useful for the prevention or control of pre-term labour.

International patent application WO 99/47549 describes diketopiperazine derivatives including 3-benzyl-2,5-diketopiperazine derivatives as inhibitors of fructose 1,6-bisphosphate (FBPase).

International patent application WO 03/053443 describes a class of diketopiperazine derivatives which exhibit a particularly useful level of activity as selective antagonists at the oxytocin receptor. A preferred class of compounds described therein is represented by the formula (A)

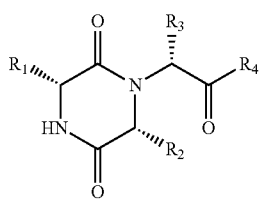

Such compounds include those wherein inter alia $R_1$ is 2-indanyl, $R_2$ is $C_{3-4}$alkyl, $R_3$ is a 5 or 6 membered heteroaryl group linked to the rest of the molecule via a carbon atom in the ring, $R_4$ represents the group $NR_5R_6$ wherein $R_5$ and $R_6$ each represent alkyl e.g. methyl, or $R_5$ and $R_6$ together with the nitrogen atom to which they are attached form a 3 to 7 membered saturated heterocyclic ring which heterocycle may contain an additional heteroatom selected from oxygen.

International patent application WO 2005/000840 describes diketopiperazine derivatives of formula (B)

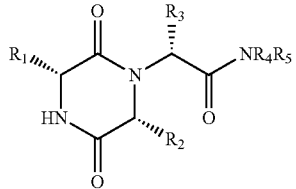

wherein $R_1$ is 2-indanyl, $R_2$ is 1-methylpropyl, $R_3$ is 2-methyl-1,3-oxazol-4-yl and $R_4$ and $R_5$ together with the nitrogen atom to which they are attached represent morpholino.

We have now found a novel group of selective oxytocin receptor antagonists which exhibit a particularly advantageous pharmacokinetic profile.

The present invention thus provides at least one chemical entity selected from compounds of formula (I)

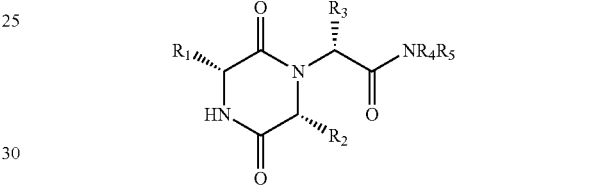

wherein $R_1$ is 2-indanyl, $R_2$ is 1-methylpropyl, $R_3$ is a group selected from 2,6-dimethyl-3-pyridyl or 4,6-dimethyl-3-pyridyl, $R_4$ represents methyl and $R_5$ represents hydrogen or methyl or $R_4$ and $R_5$ together with the nitrogen atom to which they are attached represent morpholino and pharmaceutically acceptable derivatives thereof.

It will be appreciated that the compounds of formula (I) possess the absolute stereochemistry depicted at the asymmetric carbon atoms bearing groups $R_1$, $R_2$ and $R_3$, i.e. the stereochemistry at these positions is always (R). Nevertheless, it should also be appreciated that although such compounds are substantially free of the (S)-epimer at each of $R_1$, $R_2$ and $R_3$, each epimer may be present in small amounts, for example 1% or less of the (S)-epimer may be present.

It will also be appreciated that the group $R_2$ contains an asymmetric carbon atom and that the invention includes both the (R)- and (S)-epimers thereof.

In one embodiment of the invention, $R_2$ is (1S)-1-methylpropyl. In another embodiment of the invention, $R_2$ is (1R)-1-methylpropyl.

One embodiment of the invention is the compounds the preparation of which is specifically described in examples 1, 2, 3 and 6. Another embodiment of the invention is the compounds the preparation of which is specifically described in examples 1, 2 and 3. A further embodiment of the invention is the compounds the preparation of which is specifically described in examples 3 and 6. A yet further embodiment of the invention is the compound the preparation of which is specifically described in example 3. Another embodiment of the invention is the compound the preparation of which is specifically described in example 1.

In one aspect, chemical entities useful in the present invention may be at least one chemical entity selected from:
(2R)-2-{(3R,6R)-3-(2,3-dihydro-1H-inden-2-yl)-6-[(1S)-1-methylpropyl]-2,5-dioxo-1-piperazinyl}-2-(2,6-dimethyl-3-pyridinyl)-N-methylethanamide;

(2R)-2-{(3R,6R)-3-(2,3-dihydro-1H-inden-2-yl)-6-[(1S)-1-methylpropyl]-2,5-dioxo-1-piperazinyl}-2-(2,6-dimethyl-3-pyridinyl)-N,N-dimethylethanamide;
(3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione;
(2R)-2-{(3R,6R)-3-(2,3-Dihydro-1H-inden-2-yl)-6-[(1S)-1-methylpropyl]-2,5-dioxo-1-piperazinyl}-2-(4,6-dimethyl-3-pyridinyl)-N,N-dimethylethanamide;
(2R)-2-{(3R,6R)-3-(2,3-Dihydro-1H-inden-2-yl)-6-[(1S)-1-methylpropyl]-2,5-dioxo-1-piperazinyl}-2-(4,6-dimethyl-3-pyridinyl)-N-methylethanamide; (3R,6R)-3-(2,3-dihydro-1H-inden-2-yl)-1-[(1R)-1-(4,6-dimethyl-3-pyridinyl)-2-(4-morpholinyl)-2-oxoethyl]-6-[(1S)-1-methylpropyl]-2,5-piperazinedione;
and pharmaceutically acceptable derivatives thereof.

As used herein, the term "pharmaceutically acceptable" means a compound which is suitable for pharmaceutical use. Salts and solvates of compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

As used herein, the term "pharmaceutically acceptable derivative", means any pharmaceutically acceptable salt, solvate, or prodrug e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. In one aspect, pharmaceutically acceptable derivatives are salts, solvates, esters, carbamates and phosphate esters. In another aspect, pharmaceutically acceptable derivatives are salts, solvates and esters. In a further aspect, pharmaceutically acceptable derivatives are salts and solvates. In another aspect, pharmaceutically acceptable derivatives are physiologically acceptable salts.

Suitable physiologically acceptable salts of compounds of the present invention include acid addition salts formed with physiologically acceptable inorganic acids or organic acids. Examples of such acids include hydrochloric acid, hydrobromic acid, nitric acid, phosphoric acid, sulphuric acid, sulphonic acids e.g. methanesulphonic, ethanesulphonic, benzenesulphonic and p-toluenesulphonic, citric acid, tartaric acid, lactic acid, pyruvic acid, acetic acid, succinic acid, fumaric acid and maleic acid.

The present invention also relates to solvates of the compounds of formula (I), for example hydrates, or solvates with pharmaceutically acceptable solvents including, but not limited to, alcohols, for example ethanol, iso-propanol, acetone, ethers, esters, e.g. ethyl acetate.

The compounds of the invention may also be used in combination with other therapeutic agents. The invention thus provides, in a further aspect, a combination comprising a compound of the invention or a pharmaceutically acceptable derivative thereof together with a further therapeutic agent.

When a compound of the invention or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. The compounds of the present invention may be used in combination with tocolytics or prophylactic medicines. These include, but are not limited to, beta-agonists such as terbutaline or ritodrine, calcium channel blockers, e.g. nifedepine, non-steroidal anti-inflammatory drugs, such as indomethacin, salts of magnesium, such as magnesium sulphate, other oxytocin antagonists, such as atosiban, and progesterone agonists and formulations. In addition the compounds of the present invention may be used in combination with antenatal steroids including betamethasone and dexamethasone, prenatal vitamins especially folate supplements, antibiotics, including but not limited to ampicillin, amoxicillin/clavulanate, metronidazole, clindamycin, and anxiolytics.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

The compounds of formula (I) have a high affinity for the oxytocin receptors on the uterus of rats and humans and this may be determined using conventional procedures. For example the affinity for the oxytocin receptors on the rat uterus may be determined by the procedure of Pettibone et al, Drug Development Research 30. 129-142 (1993). The compounds of the invention also exhibit high affinity at the human recombinant oxytocin receptor in CHO cells and this may be conveniently demonstrated using the procedure described by Wyatt et al. Bioorganic & Medicinal Chemistry Letters, 2001 (11) p 1301-1305.

The compounds of the invention exhibit an advantageous pharmacokinetic profile including good bioavailability coupled with good aqueous solubility. In one aspect, the compounds of the invention exhibit good potency and low intrinsic clearance. In another aspect, the compounds of the invention exhibit low intrinsic clearance.

The compounds of the invention are therefore useful in the treatment or prevention of diseases and/or conditions mediated through the action of oxytocin. Examples of such diseases and/or conditions include pre-term labour, dysmenorrhea, endometriosis and benign prostatic hyperplasia.

The compounds may also be useful to delay labour prior to elective caesarean section or transfer of the patient to a tertiary care centre, treatment of sexual dysfunction (male and female), particularly premature ejaculation, obesity, eating disorders, congestive heart failure, arterial hypertension, liver cirrhosis, nephritic or ocular hypertension, obsessive-compulsive disorder and neuropsychiatric disorders. The compounds of the invention may also be useful for improving fertility rates in animals, e.g. farm animals.

The invention therefore provides at least one chemical entity selected from a compound of formula (I) and/or pharmaceutically acceptable derivatives thereof for use in therapy, particularly for use in human and veterinary therapy, and in particular use as medicine for antagonising the effects of oxytocin upon the oxytocin receptor.

The invention also provides for the use of at least one chemical entity selected from a compound of formula (I) and/or pharmaceutically acceptable derivatives thereof for the manufacture of a medicament for antagonising the effects of oxytocin on the oxytocin receptor.

According to a further aspect, the invention also provides for a method for antagonising the effects of oxytocin upon the oxytocin receptor, comprising administering to a patient in need thereof an antagonistic amount of at least one chemical entity selected from a compound of formula (I) and/or pharmaceutically acceptable derivatives thereof.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated, the route of administration and the age and the condition of the patient and will be ultimately at the discretion of the attendant physician. In general however doses employed for adult human treatment will typically be in the range of 2 to 1000 mg per day, dependent upon the route of administration.

Thus for parenteral administration a daily dose will typically be in the range 2 to 50 mg, preferably 5 to 25 mg per day. For oral administration a daily dose will typically be within the range 10 to 1000 mg, e.g. 50 to 500 mg per day.

The desired dose may conveniently be presented in a single dose or as divided doses administered at appropriate intervals, for example as two, three, four or more sub-doses per day.

While it is possible that, for use in therapy, a compound of the invention may be administered as the raw chemical, it is preferable to present the active ingredient as a pharmaceutical formulation.

The invention thus further provides a pharmaceutical formulation comprising a compound of formula (I) and/or pharmaceutically acceptable derivatives thereof together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, inhalation or insufflation, implant, vaginal or rectal administration.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; solubilizers such as surfactants for example polysorbates or other agents such as cyclodextrins; and preservatives, for example, methyl or propyl p-hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in the conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

The compositions according to the invention may contain between 0.1-99% of the active ingredient, conveniently from 1-50% for tablets and capsules and 3-50% for liquid preparations.

The advantageous pharmacokinetic profile of the compounds of the invention is readily demonstrated using conventional procedures for measuring the pharmacokinetic properties of biologically active compounds.

The compounds of the invention and pharmaceutically acceptable derivatives thereof may be prepared by the processes described hereinafter, said processes constituting a further aspect of the invention. In the following description, the groups are as defined above for compounds of the invention unless otherwise stated.

Compounds of formula (I) may be prepared by reaction of the carboxylic acid (II), wherein $R_1$, $R_2$ and $R_3$ have the meanings defined in formula (I), and the chirality at $R_3$ is either R or S, or a mixture thereof,

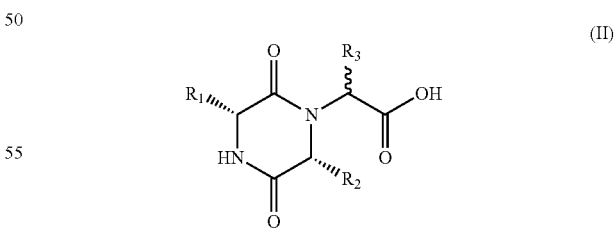

or an activated derivative thereof with the amine $HNR_4R_5$, wherein $R_4$ and $R_5$ have the meaning defined in formula (I), under standard conditions for preparing amides from a carboxylic acid or an activated derivative thereof and an amine.

It will be appreciated that the mixture of diastereomers of compounds of formula (I) obtained from the above reaction may be separated using standard resolution techniques well known in the art, for example column chromatography.

Thus the amide of formula (I) may be prepared by treating the carboxylic acid of formula (II) with an activating agent such as BOP (benzotriazol-1-yloxy-tris(dimethylamino) phosphonium hexafluorophosphate), TBTU (2-(1H-benzotriazol-1-yl)-1,1,3,3-tetramethyluronium tetrafluoroborate), BOP-Cl (bis(2-oxo-3-oxazolidinyl)phosphinic chloride), oxalyl chloride or 1,1'-carbonyldiimidazole in an aprotic solvent such as dichloromethane optionally in the presence of a tertiary amine such as triethylamine and subsequent reaction of the product thus formed, i.e. the activated derivative of the compound of formula (II), with the amine $HNR_4R_5$.

Alternatively the amide of formula (I) may be prepared by reacting a mixed anhydride derived from the carboxylic acid (II), wherein $R_1$, $R_2$ and $R_3$ have the meanings defined in formula (I) with the amine $HNR_4R_5$ in an aprotic solvent such as tetrahydrofuran.

Conveniently the reaction is carried out at low temperatures, for example 25° C. to −90° C., conveniently at approximately −78° C.

The mixed anhydride is conveniently prepared by reacting the carboxylic acid (II) with a suitable acid chloride e.g. pivalolyl chloride in an aprotic solvent such as ethyl acetate in the presence of a tertiary organic base such as a trialkylamine e.g. triethylamine and at low temperatures, for example 25° C. to −90° C., conveniently at approximately −78° C.

Compounds of formula (I) may also be prepared by reacting a compound of formula (III)

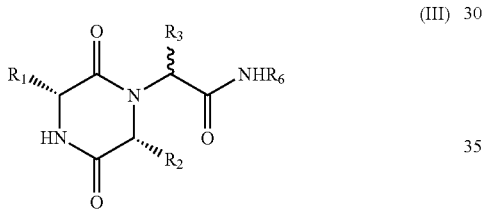
(III)

wherein $R_1$, $R_2$ and $R_3$ have the meanings defined in formula (I) and $R_6$ is 2-hydroxyphenyl, with 1,1'-carbonyldiimidazole or 1,1'-thiocarbonyldiimidazole in a suitable solvent such as dichloromethane and subsequent reaction of the products thus formed with the amine $HNR_4R_5$.

Compounds of formula (II) may be prepared from a compound of formula (III) wherein $R_6$ is 2-hydroxyphenyl by reaction with 1,1'-carbonyldiimidazole or 1,1'-thiocarbonyldiimidazole in a suitable solvent such as dichloromethane and subsequent reaction of the product thus formed with aqueous acetone.

Compounds of formula (III) wherein $R_6$ is 2-hydroxyphenyl may be prepared from the corresponding compounds of formula (III) wherein $R_6$ is a 2-benzyloxyphenyl group by hydrogenolysis using hydrogen and a palladium catalyst.

Alternatively compounds of formula (III) wherein $R_6$ is a 2-hydroxyphenyl may be prepared from the compound of formula (IV)

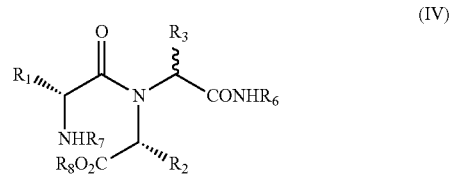
(IV)

wherein $R_1$, $R_2$ and $R_3$ have the meanings defined in formula (I), $R_6$ is 2-benzyloxyphenyl, $R_7$ is benzyloxycarbonyl and $R_8$ is $C_{1-6}$alkyl, by the reaction with hydrogen in the presence of a palladium on charcoal catalyst and acetic acid. This reaction is conveniently carried out in a solvent such as ethanol, trifluoroethanol or mixtures thereof.

Compounds of formula (IV) may be prepared by reacting the amino ester hydrochloride (V)

(V)

wherein $R_1$ has the meaning defined in formula (I) and $R_8$ is $C_{1-6}$alkyl, with an aldehyde $R_3CHO$ (VI) wherein $R_3$ has the meaning defined in formula (I), in the presence of triethylamine and in a solvent such as trifluoroethanol and then reacting the resultant product with a compound of formula (VII)

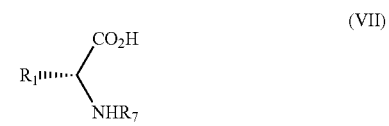
(VII)

wherein $R_1$ has the meaning defined in formula (I) and $R_7$ is t-butyloxycarbonyl or benzyloxycarbonyl and the isocyanide $CNR_6$ (VIII) wherein $R_6$ is a 2-benzyloxyphenyl group, in a solvent such as trifluoroethanol.

Compounds of formula (III) wherein $R_6$ is a 2-benzyloxyphenyl group may be prepared from a compound of formula (IV) wherein $R_1$, $R_2$ and $R_3$ have the meanings defined in formula (I), $R_6$ is 2-benzyloxyphenyl and $R_7$ is t-butyloxycarbonyl by the reaction with hydrogen chloride in dioxan followed with triethylamine in a solvent such as dichloromethane.

The compound of formula (IV) wherein $R_7$ is t-butyloxycarbonyl may be prepared by the route described above using a compound of formula (VII) wherein $R_7$ is t-butyloxycarbonyl.

The $R_2$ substituent is a 1-methylpropyl group and the compound of formula (I) wherein $R_2$ is a 1-methylpropyl group having an (S) or (R) configuration may be prepared by starting with the aminoester hydrochloride (V) wherein the $R_2$ group has the required (S) or (R) configuration.

Aminoester hydrochloride (V), wherein $R_1$ has the meaning defined in formula (I) and $R_8$ is $C_{1-6}$ alkyl, may be prepared from the corresponding commercially available amino acids, D-alloisoleucine or D-isoleucine, by the method of Schmidt, U; Kroner, M; Griesser, H. Synthesis (1989), (11), 832-5.

Aldehydes R₃CHO (VI), wherein R₃ has the meaning defined in formula (I), are either commercially available or may be prepared by literature methods (Comins, Daniel L.; Weglarz, Michael A.; J. Org. Chem.; 53; 19; 1988; 4437-4442).

The aminoacid derivative (VII) wherein $R_1$ has the meaning defined in formula (I) and $R_7$ is t-butyloxycarbonyl is commercially available; the aminoacid derivative (VII) wherein $R_1$ has the meaning defined in formula (I) and $R_7$ is benzyloxycarbonyl may be prepared from the corresponding commercially available amino acid $(R)—R_1CH(NH_2)CO_2H$ (IX), wherein $R_1$ has the meaning defined in formula (I), by treatment with N-(benzyloxycarbonyloxy)succinimide and triethylamine in a solvent such as dioxane in water.

The isocyanide $CNR_6$ (VIII) may be prepared according to literature methods (Obrecht, Roland; Herrmann, Rudolf; Ugi, Ivar, *Synthesis*, 1985, 4, 400-402).

Acid addition salts of the compound of formula (I) may be prepared by conventional means, for example, by treating a solution of the compound in a suitable solvent such as dichloromethane or acetone, with a suitable solution of the appropriate inorganic or organic acid.

The following examples are illustrative, but not limiting of the embodiments of the present invention.

EXPERIMENTAL

Nomenclature

All intermediates and examples were named using ACD Name Pro 6.02 in ISISDraw.

Abbreviations

CV: Column volume. One column volume is defined as the volume occupied by the sorbent in the packed column. This can be approximately calculated from the mass and density of the particular sorbent being used (1CV=mass divided by density).

General Purification and Analytical Methods

Analytical HPLC was conducted on a Supelcosil LCABZ+ PLUS column (3.3 cm×4.6 mm ID), eluting with 0.1% $HCO_2H$ and 0.01 M ammonium acetate in water (solvent A), and 0.05% $HCO_2H$ and 5% water in acetonitrile (solvent B), using the either elution gradient 1, 0-0.7 minutes 0% B, 0.7-4.2 minutes 0%-100% B, 4.2-5.3 minutes 100% B, 5.3-5.5 minutes 0% B or elution gradient 2, 0-0.7 minutes 0% B, 0.7-4.2 minutes 0%-100% B, 4.2-4.6 minutes 100% B, 4.6-4.8 minutes 0% B at a flow rate of 3 ml/minute. Retention times (Rt) are quoted in minutes. The mass spectra (MS) were recorded on a Waters ZQ 2000 mass spectrometer using electrospray positive [ES+ve to give $MH^+$ and $M(NH_4)^+$ molecular ions] or electrospray negative [ES-ve to give $(M-H)^-$ molecular ion] modes. $^1H$ NMR spectra were recorded using a Bruker DPX 400 MHz spectrometer using tetramethylsilane as the external standard.

Purification using silica cartridges refers to chromatography carried out using a Combiflash® Companion™ with Redisep® cartridges supplied by Presearch. Hydrophobic frits refer to filtration tubes sold by Whatman. SPE (solid phase extraction) refers to the use of cartridges sold by International Sorbent Technology Ltd. TLC (thin layer chromatography) refers to the use of TLC plates sold by Merck coated with silica gel 60 $F_{254}$.

Intermediate 1

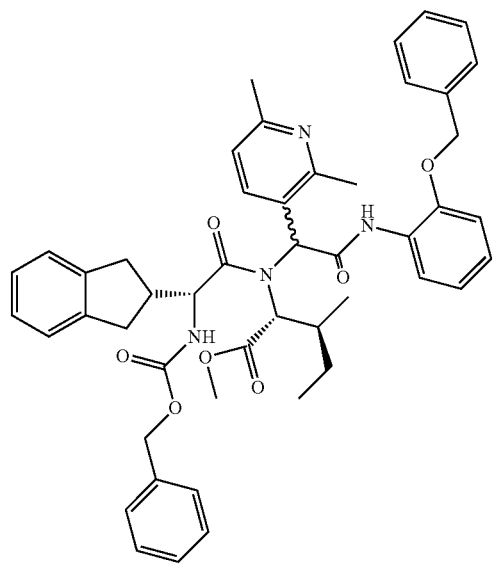

Methyl N-[(2R)-2-(2,3-dihydro-1H-inden-2-yl)-2-({[(phenylmethyl)oxy]carbonyl}amino)acetyl]-N-[1-(2,6-dimethyl-3-pyridinyl)-2-oxo-2-({2-[(phenylmethyl)oxy]phenyl}amino)ethyl]-D-alloisoleucinate 2,6-dimethylpyridine-3-carboxaldehyde (Aurora Feinchemie GmbH) (2.00 g, 16.1 mmol) and (D)-alloisoleucine methyl ester hydrochloride (2.93 g, 16.1 mmol) in methanol (50 mL) and 2,2,2-trifluoroethanol (50 mL) were treated with triethylamine (2.24 mL, 16.1 mmol) and the mixture was stirred under nitrogen at room temperature for 20 h. (2R)-2,3-dihydro-1H-inden-2-yl({[(phenylmethyl)oxy]carbonyl}amino)ethanoic acid (5.24 g, 16.1 mmol) and 2-benzyloxyphenylisonitrile (3.37 g, 16.1 mmol) were added and the mixture was stirred at room temperature under nitrogen for 4 days. The mixture was concentrated under reduced pressure then partitioned between ethyl acetate (150 mL) and water (150 mL) plus saturated aqueous sodium hydrogen carbonate (6 mL). The aqueous phase was back-extracted with ethyl acetate (50 mL) and the combined organic extracts were washed successively with semi-saturated aqueous solutions of sodium hydrogen carbonate, ammonium chloride and sodium chloride (100 mL each), dried over anhydrous magnesium sulphate and evaporated under reduced pressure to give the crude product (12.01 g). This was purified on a Redisep silica column (330 g) eluted with 20-50% ethyl acetate in cyclohexane to afford 7.46 g of the title compound as a pair of diastereomers.

HPLC Rt=3.88 and 3.96 minutes (gradient 1); m/z $[M+H]^+=797$

Intermediate 2

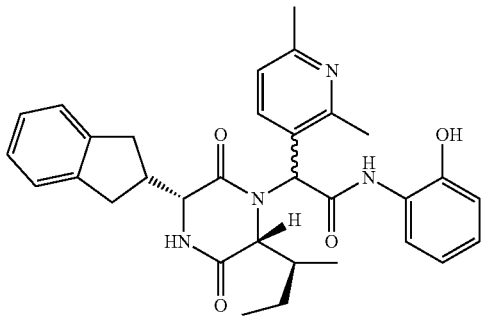

2-{(3R,6R)-3-(2,3-dihydro-1H-inden-2-yl)-6-[(1S)-1-methylpropyl]-2,5-dioxo-1-piperazinyl}-2-(2,6-dimethyl-3-pyridinyl)-N-(2-hydroxyphenyl)acetamide The crude methyl N-[(2R)-2-(2,3-dihydro-1H-inden-2-yl)-2-({[(phenylmethyl)oxy]carbonyl}amino)acetyl]-N-[1-(2,6-dimethyl-3-pyridinyl)-2-oxo-2-({2-[(phenylmethyl)oxy]phenyl}amino)ethyl]-D-alloisoleucinate (intermediate 1) (7.46 g) was dissolved in ethanol (150 mL) and acetic acid (10 mL) and the mixture was hydrogenated at 1 atmosphere of $H_2$ over 10% palladium on carbon (Degussa type) (1.8 g wetted with water 1:1 w:w) for 18 h. The reaction mixture was evaporated under reduced pressure and the residue was partitioned between ethyl acetate and water with saturated aqueous sodium hydrogen carbonate added until the aqueous phase was basic (pH 8). The aqueous phase was extracted with ethyl acetate and the combined organic extracts were washed with saturated aqueous sodium hydrogen carbonate:water 3:1 (100 mL) then with saturated brine before being dried over anhydrous magnesium sulphate and evaporated under reduced pressure. The crude product was purified on a Redisep silica column (120 g) eluted with 0-10% methanol in ethyl acetate to give the title compound as a pair of diastereomers (2.94 g).

HPLC Rt=2.75 and 2.81 minutes (gradient 2); m/z [M+H]$^+$= 541

Intermediate 3

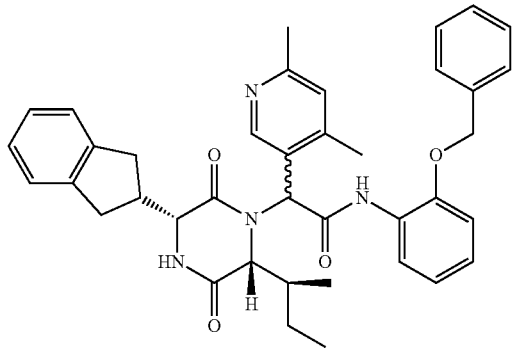

2-{(3R,6R)-3-(2,3-Dihydro-1H-inden-2-yl)-6-[(1S)-1-methylpropyl]-2,5-dioxo-1-piperazinyl}-2-(4,6-dimethyl-3-pyridinyl)-N-{2-[(phenylmethyl)oxy]phenyl}acetamide 4,6-Dimethyl-3-pyridinecarbaldehyde[1] (2.52 g) and methyl D-alloisoleucinate hydrochloride (3.4 g) were dissolved in 2,2,2-trifluoroethanol (50 ml). To this was added triethylamine (2.61 ml) and the reaction mixture was left to stand for 18 hours. (2R)-2,3-Dihydro-1H-inden-2-yl({[(1,1-dimethylethyl)oxy]-carbonyl}amino)ethanoic acid (5.44 g) and 2-[(phenylmethyl)oxy]phenyl isocyanide (4.18 g) with methanol (10 ml) were added to the reaction mixture and the solution was stirred at room temperature for 3 days. The solvent was removed in vacuo and the residue was separated between dichloromethane and water. The organic phase was passed through a hydrophobic frit and evaporated in vacuo. The residue was dissolved in 4N hydrogen chloride in dioxan (50 ml) and the reaction mixture was left to stand for 4 hours. The solvent was removed in vacuo and the residue was dissolved in dichloromethane (200 ml). To this was added triethylamine (20 ml) and the reaction mixture was left to stand for 20 hours. The reaction mixture was separated between dichloromethane and water. The organic phase was passed through a hydrophobic frit and evaporated in vacuo. The residue was applied to 4×90 g Biotage columns and eluted with cyclohexane/ethyl acetate (1:1, 1:2 v/v) and ethyl acetate. The required fractions were combined and evaporated in vacuo to give 2-{(3R,6R)-3-(2,3-dihydro-1H-inden-2-yl)-6-[(1S)-1-methylpropyl]-2,5-dioxo-1-piperazinyl}-2-(4,6-dimethyl-3-pyridinyl)-N-{2-[(phenylmethyl)oxy]phenyl}acetamide (5.55 g, 47%) as a tan foam.

HPLC Rt=3.43, 3.45 minutes gradient 1); m/z [M+H]$^+$= 631

REF

1. Comins, Daniel L.; Weglarz, Michael A.; J. Org. Chem.; 53; 19; 1988; 4437-4442.

Intermediate 4

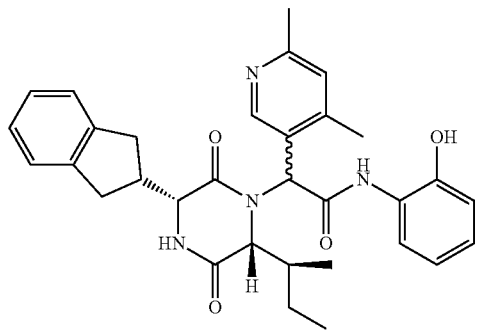

2-{(3R,6R)-3-(2,3-Dihydro-1H-inden-2-yl)-6-[(1S)-1-methylpropyl]-2,5-dioxo-1-piperazinyl}-2-(4,6-dimethyl-3-pyridinyl)-N-(2-hydroxyphenyl)acetamide 2-{(3R,6R)-3-(2,3-Dihydro-1H-inden-2-yl)-6-[(1S)-1-methylpropyl]-2,5-dioxo-1-piperazinyl}-2-(4,6-dimethyl-3-pyridinyl)-N-{2-[(phenylmethyl)oxy]phenyl}acetamide (intermediate 3) (3.30 g) was dissolved in ethanol (75 ml) and hydrogenated over palladium on charcoal (wet 10% Pd, 0.50 g) for 20 hours. The catalyst was removed by filtration and washed with dichloromethane. The combined filtrate and washings were evaporated in vacuo. The residue was applied to a 90 g Biotage column and eluted with ethyl acetate. The required fractions were combined and evaporated in vacuo to give 2-{(3R,6R)-3-(2,3-dihydro-1H-inden-2-yl)-6-[(1S)-1-methylpropyl]-2,5-dioxo-1-piperazinyl}-2-(4,6-dimethyl-3-pyridinyl)-N-(2-hydroxyphenyl)acetamide (2.43 g, 87%) as a pale yellow solid.

HPLC Rt=2.86 minutes (gradient 1); m/z [M+H]⁺=541.

Intermediate 5

{(3R,6R)-3-(2,3-Dihydro-1H-inden-2-yl)-6-[(1S)-1-methylpropyl]-2,5-dioxo-1-piperazinyl}(2,6-dimethyl-3-pyridinyl)acetic acid hydrochloride

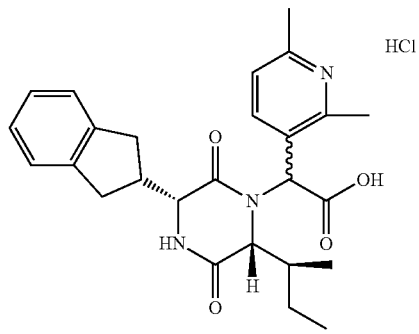

2-{(3R,6R)-3-(2,3-dihydro-1H-inden-2-yl)-6-[(1S)-1-methylpropyl]-2,5-dioxo-1-piperazinyl}-2-(2,6-dimethyl-3-pyridinyl)-N-(2-hydroxyphenyl)acetamide (24.25 g, 45 mmol) (intermediate 2) and 1,1'-carbonyldiimidazole (11.7 g, 72 mmol) were dissolved in dry dichloromethane (200 ml) and left to stand under nitrogen for 20 hours. The solvent was removed in vacuo and the residue was dissolved in acetone (200 ml) and 2N hydrochloric acid (20 ml). After stirring for 20 hours the solvent was removed in vacuo and the residue was dissolved in methanol (50 ml). The solution was applied to an aminopropyl cartridge (2×70 g) and eluted with methanol (250 ml) and then 10% acetic acid in methanol (250 ml). The required fractions were combined and evaporated in vacuo. The residue was treated with 2N hydrochloric acid and the resulting solution evaporated in vacuo to give the title compound {(3R,6R)-3-(2,3-dihydro-1H-inden-2-yl)-6-[(1S)-1-methylpropyl]-2,5-dioxo-1-piperazinyl}(2,6-dimethyl-3-pyridinyl)acetic acid hydrochloride as a tan solid (12.21 g, 56%).

HPLC Rt=2.48 minutes (gradient 2); m/z [M+H]⁺=450.

Intermediate 6

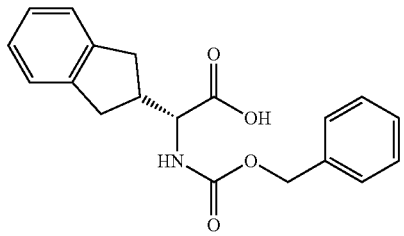

(2R)-2,3-dihydro-1H-inden-2-yl({[(phenylmethyl)oxy]carbonyl}amino)ethanoic acid (2R)-amino(2,3-dihydro-1H-inden-2-yl)ethanoic acid (1.91 g, 10 mmol) was suspended in dioxane (10 ml) and water (10 ml). To this was added triethylamine (1.7 ml) and N-(benzyloxycarbonyloxy)-succinimide (2.54 g) and the reaction mixture was stirred rapidly at room temperature for 2 days. The reaction mixture was poured into water (50 ml) and extracted with chloroform (100 ml). The organic phase was washed with 1N hydrochloric acid (50 ml) and water (50 ml). This was dried over magnesium sulphate and the solvent removed in vacuo to give the title compound (3.06 g, 94%):
¹H NMR (CDCl₃) δ 7.40-7.29 (m, 5H), 7.21-7.11 (m, 4H), 5.28 (d, 1H, J=8.6 hZ), 5.11 (s, 2H), 4.57 (m, 1H), 3.14-2.79 (m, 5H); LCMS m/z 326 (MH⁺), Rt 3.35 min (gradient 2)

Example 1

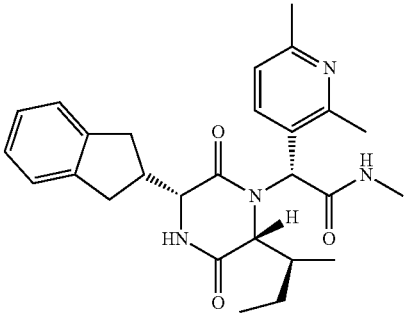

(2R)-2-{(3R,6R)-3-(2,3-Dihydro-1H-inden-2-yl)-6-[(1S)-1-methylpropyl]-2,5-dioxo-1-piperazinyl}-2-(2,6-dimethyl-3-pyridinyl)-N-methylethanamide 2-{(3R,6R)-3-(2,3-dihydro-1H-inden-2-yl)-6-[(1S)-1-methylpropyl]-2,5-dioxo-1-piperazinyl}-2-(2,6-dimethyl-3-pyridinyl)-N-(2-hydroxyphenyl)acetamide (intermediate 2) (0.400 g, 0.74 mmol) and 1,1'-carbonyldiimidazole (0.192 g, 1.18 mmol) in dry dichloromethane (10 mL) were stirred at room temperature under N₂ for 7 hrs. The mixture was treated with a 2M solution of methylamine in tetrahydrofuran (1.849 mL, 3.70 mmol) and left to stand overnight at room temperature. The solvents were blown down under N₂ and the residue was purified on a Redisep silica column (35 g) eluted with 0-10% methanol in ethyl acetate followed by further purification on a Kromasil KR100-10-C18 reverse-phase column eluted with aqueous acetonitrile (20-45% MeCN) containing 0.1% formic acid. This gave the title compound as a white lyophilisate (30%) after freeze-drying from 1,4-dioxane.

HPLC Rt=2.44 minutes (gradient 1); m/z [M+H]$^+$=463

$^1$H NMR (CDCl$_3$) δ 7.63 (d, 1H), 7.25-7.15 (m, 4H), 7.05 (d, 1H), 6.79 (d, 1H), 5.96 (q, 1H), 5.35 (s, 1H), 4.07 (dd, 1H), 3.88 (d, 1H), 3.19-2.88 (m, 4H), 2.85 (d, 3H), 2.81-2.73 (m, 1H), 2.56 (s, 3H), 2.55 (s, 3H), 1.82-1.67 (m, 2H), 1.20-1.08 (m, 1H), 0.99 (d, 3H), 0.90 (t, 3H).

Similarly prepared from intermediate 2 and dimethylamine (2.0M in tetrahydrofuran):

Example 2

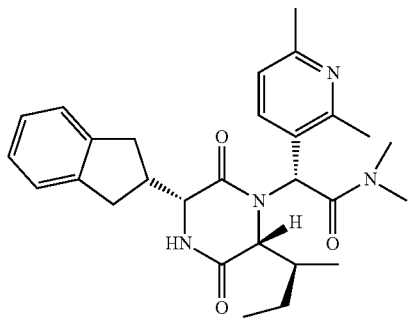

(2R)-2-{(3R,6R)-3-(2,3-Dihydro-1H-inden-2-yl)-6-[(1S)-1-methylpropyl]-2,5-dioxo-1-piperazinyl}-2-(2,6-dimethyl-3-pyridinyl)-N,N-dimethylethanamide as a white lyophilisate (33%) after freeze-drying from 1,4-dioxane HPLC Rt=2.69 minutes (gradient 1); m/z [M+H]$^+$=477

$^1$H NMR (CDCl$_3$) δ 7.49 (d, 1H), 7.27-7.15 (m, 4H), 7.08 (d, 1H), 6.66 (s, 1H), 6.30 (d, 1H), 4.10 (dd, 1H), 4.05 (d, 1H), 3.22-3.08 (m, 3H), 2.99-2.84 (m, 4H), 2.80-2.70 (m, 4H), 2.63 (s, 3H), 2.58 (s, 3H), 1.65-1.53 (m, 1H), 0.97-0.78 (m, 2H), 0.71 (t, 3H), 0.46 (d, 3H).

Similarly prepared from intermediate 2 and morpholine (3.7 mmol):

Example 3

Method A

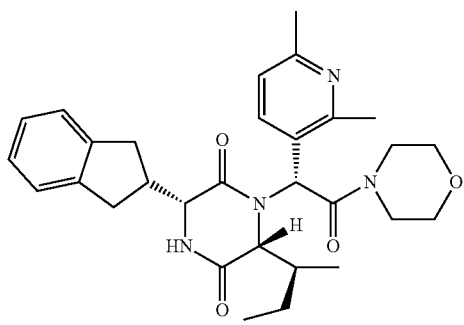

(3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione as a white lyophilisate (88 mg, 23%) after freeze-drying from 1,4-dioxane HPLC Rt=2.70 minutes (gradient 2); m/z [M+H]$^+$=519

$^1$H NMR (CDCl$_3$) δ 7.49 (d, 1H), 7.27-7.15 (m, 4H), 7.10 (d, 1H), 6.68 (s, 1H), 6.40 (d, 1H), 4.10 (dd, 1H), 4.01 (d, 1H), 3.74-3.52 (m, 5H), 3.28-3.07 (m, 5H), 2.97-2.84 (m, 2H), 2.79-2.71 (m, 1H), 2.62 (s, 3H), 2.59 (s, 3H), 1.65-1.53 (m, 1H), 0.98-0.80 (m, 2H), 0.70 (t, 3H), 0.45 (d, 3H).

Example 3

Method B

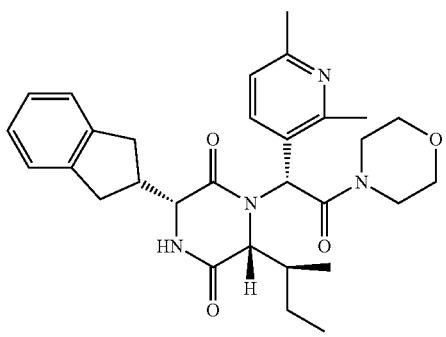

(3R,6R)-3-(2,3-Dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione A suspension of {(3R,6R)-3-(2,3-dihydro-1H-inden-2-yl)-6-[(1S)-1-methylpropyl]-2,5-dioxo-1-piperazinyl}(2,6-dimethyl-3-pyridinyl)acetic acid hydrochloride (5.0 g, 10.3 mmol) (intermediate 5) in dry dichloromethane (50 ml) was treated with 1,1-carbonyldiimidazole (2.6 g, 16 mmol) and the reaction mixture was stirred under nitrogen for 18 hours. Morpholine (4.8 ml, 55 mmol) was added and the resultant solution was left to stand under nitrogen for 18 hours. The solvent was removed in vacuo and the residue was separated between ethyl acetate and water. The organic phase was washed with brine and dried over anhydrous magnesium sulphate. The solvent was removed in vacuo and the residue was dissolved in dichloromethane. This was applied to a basic alumina cartridge (240 g) and eluted using a gradient of 0-7.5% methanol in diethyl ether (9CV), 7.5-10% methanol in diethyl ether (1CV) and 10% methanol in diethyl ether (1CV). The required fractions were combined and evaporated in vacuo to give (3R,6R)-3-(2,3-dihydro-1H-inden-2-yl)-1-[(1R)-1-(2,6-dimethyl-3-pyridinyl)-2-(4-morpholinyl)-2-oxoethyl]-6-[(1S)-1-methylpropyl]-2,5-piperazinedione as a white solid (2.4 g, 45%).

HPLC Rt=2.72 minutes (gradient 2); m/z [M+H]$^+$=519

Example 4

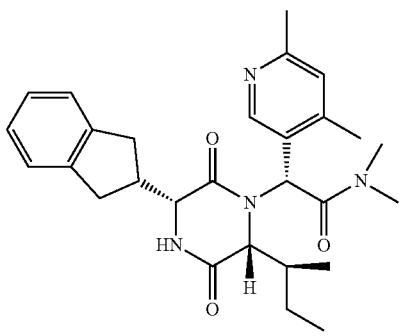

(2R)-2-{(3R,6R)-3-(2,3-Dihydro-1H-inden-2-yl)-6-[(1S)-1-methylpropyl]-2,5-dioxo-1-piperazinyl}-2-(4,6-dimethyl-3-pyridinyl)-N,N-dimethylethanamide 2-{(3R,6R)-3-(2,3-Dihydro-1H-inden-2-yl)-6-[(1S)-1-methylpropyl]-2,5-dioxo-1-piperazinyl}-2-(4,6-dimethyl-3-pyridinyl)-N-(2-hydroxyphenyl)acetamide (intermediate 4) (0.700 g) and 1,1'-carbonyldiimidazole (0.324 g) were dissolved in dry dichloromethane (20 ml) and left to stand for 20 hours. To one half of this solution (10 ml) was added a 2.0M solution of dimethylamine in tetrahydrofuran (5 ml) and the reaction mixture was left to stand for 3 days. The reaction mixture was separated between dichloromethane and saturated aqueous sodium bicarbonate solution. The organic phase was passed through a hydrophobic frit and evaporated in vacuo. The residue was applied to a silica cartridge (10 g) and eluted with ethyl acetate then 5% methanol in ethyl acetate. The required fractions were evaporated in vacuo and the residue was purified further using Mass Directed AutoPrep. This gave (2R)-2-{(3R,6R)-3-(2,3-Dihydro-1H-inden-2-yl)-6-[(1S)-1-methylpropyl]-2,5-dioxo-1-piperazinyl}-2-(4,6-dimethyl-3-pyridinyl)-N,N-dimethylethanamide (0.10 g, 32%) as a white foam.

HPLC Rt=2.82 minutes (gradient 1); m/z [M+H]$^+$=477

$^1$H NMR (CDCl$_3$) δ 8.32 (s, 1H), 7.26-7.15 (m, 4H), 7.08 (s, 1H), 6.71 (s, 1H), 6.16 (d, 1H), 4.17 (d, 1H), 4.10 (dd, 1H), 3.22-3.06 (m, 3H), 2.98 (s, 3H), 2.91 (m, 1H), 2.74 (dd, 1H), 2.67 (s, 3H), 2.57 (s, 3H), 2.39 (s, 3H), 1.56 (m, 1H), 0.93 (m, 1H), 0.85 (m, 1H), 0.68 (t, 3H), 0.45 (d, 3H).

Similarly prepared from intermediate 4 and methylamine:

Example 5

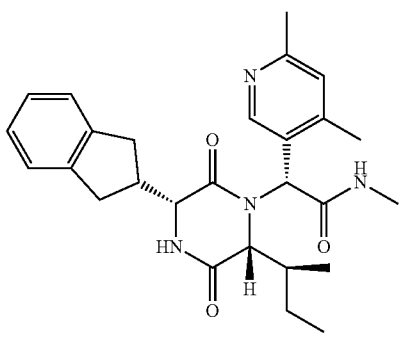

(2R)-2-{(3R,6R)-3-(2,3-Dihydro-1H-inden-2-yl)-6-[(1S)-1-methylpropyl]-2,5-dioxo-1-piperazinyl}-2-(4,6-dimethyl-3-pyridinyl)-N-methylethanamide HPLC Rt=2.60 minutes (gradient 1); m/z [M+H]$^+$=463

$^1$H NMR (CDCl$_3$) δ 8.48 (s, 1H), 7.25-7.14 (m, 4H), 7.04 (s, 1H), 6.72 (d, 1H), 6.07 (q, 1H), 5.45 (s, 1H), 4.07 (dd, 1H), 3.90 (d, 1H), 3.17-3.04 (m, 3H), 2.92 (m, 1H), 2.86 (d, 3H), 2.76 (dd, 1H), 2.53 (s, 3H), 2.33 (s, 3H), 1.70 (m, 2H), 1.12 (m, 1H), 0.94 (d, 3H), 0.87 (t, 3H).

Similarly prepared from intermediate 4 and morpholine:

Example 6

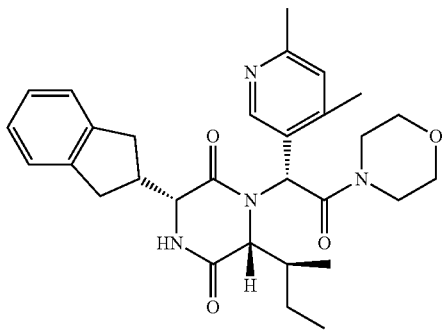

(3R,6R)-3-(2,3-dihydro-1H-inden-2-yl)-1-[(1R)-1-(4,6-dimethyl-3-pyridinyl)-2-(4-morpholinyl)-2-oxoethyl]-6-[(1S)-1-methylpropyl]-2,5-piperazinedione HPLC Rt=2.94 minutes (gradient 2); m/z [M+H]$^+$=519

$^1$H NMR (CDCl$_3$) δ 8.34 (s, 1H), 7.25-7.15 (m, 4H), 7.09 (s, 1H), 6.71 (s, 1H), 6.21 (d, 1H), 4.14-4.07 (m, 2H), 3.73-3.47 (m, 5H), 3.23-3.05 (m, 5H), 2.95-2.83 (m, 2H), 2.74 (dd, 1H), 2.58 (s, 3H), 2.38 (s, 3H), 1.56 (m, 1H), 0.94 (m, 1H), 0.86 (m, 1H), 0.68 (t, 3H), 0.44 (d, 3H).

Biological Activity

Examples 1-6 of the present invention were tested in all of the assays described below. Results for each of the compounds are shown in Table 1 below. Table 1 also includes a compound X for comparison.

Assay 1

Determination of Antagonist Affinity at Human Oxytocin-1 Receptors Using FLIPR

Cell Culture

Adherent Chinese Hamster Ovary (CHO) cells, stably expressing the recombinant human Oxytocin-1 (hOT) receptor, were maintained in culture in DMEM:F12 medium (Sigma, cat no D6421), supplemented with 10% heat inactivated foetal calf serum (Gibco/Invitrogen, cat. no. 01000-147), 2 mM L-glutamine (Gibco/Invitrogen, cat. no. 25030-024) and 0.2 mg/ml G418 (Gibco/Invitrogen, cat no. 10131-027). Cells were grown as monolayers under 95%:5% air:CO$_2$ at 37° C. and passaged every 3-4 days using TrypLE™ Express (Gibco/Invitrogen, cat no. 12604-013).

Measurement of $[Ca^{2+}]_i$ Using the FLIPR™

CHO-hOT cells were seeded into black walled clear-base 384-well plates (Nunc) at a density of 10,000 cells per well in culture medium as described above and maintained overnight (95%:5% air:$CO_2$ at 37° C.). After removal of culture medium, cells were incubated for 1 h at 37° C. in Tyrode's medium (NaCl, 145 mM; KCl, 2.5 mM; HEPES, 10 mM; Glucose, 10 mM; $MgCl_2$, 1.2 mM; $CaCl_2$, 1.5 mM) containing probenacid (0.7 mg/ml), the cytoplasmic calcium indicator, Fluo-4 (4 uM; Teflabs, USA) and the quenching agent Brilliant Black (250 uM; Molecular Devices, UK). Cells were then incubated for an additional 30 min at 37° C. with either buffer alone or buffer containing OT antagonist, before being placed into a FLIPR™ (Molecular Devices, UK) to monitor cell fluorescence ($\lambda_{ex}$=488 nm, $\lambda_{EM}$=540 nm) before and after the addition of a submaximal concentration of oxytocin (EC80).

Data Analysis

Functional responses using FLIPR were analysed using Activity Base Version 5.0.10.

Assay 2
Oxytocin Binding Assay
Preparations

Membranes were prepared from CHO cells expressing human recombinant oxytocin receptors. The membrane preparation was frozen in aliquots at −70° C. until used.

Binding Assay Protocol

Membranes (~50 ug) were incubated in 200 ul of assay buffer (50 mM Tris, 10 mM $MgCl_2$, and 0.1% bovine serum albumin, pH 7.5) containing ~2.4 nM of [3H]-oxytocin in the absence (total binding) or presence (non-specific binding) of 1 uM unlabeled oxytocin and increasing concentrations of the compounds in Examples 1 to 6 or comparator compounds. Incubations were performed at room temperature for 60 minutes. The reactions were stopped with 3 ml of ice cold buffer and filtered through Whatman GF/C filter paper presoaked in 0.3% polyethylenimine. The filters were washed 4 times with 3 ml buffer using a Brandel cell harvester. The filters were counted in 3 ml Ready Safe scintillation fluid (Beckman).

Specific binding represented approximately 90% of total binding.

Data Analysis $IC_{50}$ values were determined from competition binding experiments using non-linear regression analysis (GraphPad) and converted to Ki using the method of Cheng and Prusoff, 1974. Data are reported as mean values.

Assay 3
Determination of In Vitro Intrinsic Clearance in Microsomes

NADP regeneration buffer for use in incubations was prepared fresh on the assay day. It contained 7.8 mg glucose-6-phosphate (mono-sodium salt), 1.7 mg NADP and 6 Units glucose-6-phosphate dehydrogenase per 1 mL of 2% sodium bicarbonate. Microsomes (human, female; cynomolgus monkey, female; dog, female; rat, female) were prepared in pH7.4 phosphate buffer and contained 0.625 mg protein/mL. Unless stated, all subsequent steps were performed by a Tecan Genesis 150/8 RSP. A 1.25 mM stock solution of the compounds was prepared in Acetonitrile/water (1:1). 25 ul of the 1.25 mM stock solution was added to 600 ul of Acetonitrile/water (1:1) to give a 50 uM solution. For each species, the 50 uM solutions (10 uL) were added to microsomes (790 uL) in a microplate (Porvair, 96 deepwell, square). 400 uL of the microsomal solution containing the compound was transferred to a microplate (Porvair, 96 deepwell, round) and was pre-warmed at 37° C. for five minutes prior to initiation of incubations. All incubations were initiated by addition of 100 uL of NADP regeneration system to the pre-warmed microsomes. The mixtures were incubated at 37° C. in a Techne heating block. Following 0, 3, 6, 12 and 30 minutes incubation, 20 uL aliquots were taken and added to 100 uL of acetonitrile containing internal standard.

For determination of the rate of metabolism, incubations were performed at a compound concentration of 0.5 uM and a protein concentration of 0.5 mg/mL. The concentration of solvent in the incubation was 0.5%.

Test compound concentrations were determined by LC/MS/MS; results were reported as analyte:internal standard peak area ratios.

The rate of disappearance was calculated by fitting a single exponential decay to the concentration-time curve using Excel and intrinsic clearance was calculated using the following formula:

$$Cli = \frac{[\text{rate } (1/\text{min}) * 52.5 \text{ mg protein/g liver}]}{0.5 \text{ mg protein/mL}}$$

Results

Examples 1 to 6 of the present invention and also a comparator compound X=(2R)-2-[(3R,6R)-3-(2,3-dihydro-1H-inden-2-yl)-6-isobutyl-2,5-dioxopiperazin-1-yl]-N,N-dimethyl-2-(6-methylpyridin-3-yl)ethanamide (Example 209 in WO 03/053443) were tested in the above assays.

Comparator compound X when tested in assays 1 and 2 showed a similar potency to that exhibited by Compounds 1 to 6 of the present invention, in fact each of these compounds exhibited fpKi's of between 8.1 and 9.2 (Assay 1) and pKi's of between 8.8 and 10.5 (Assay 2).

However, the compounds of the present invention exhibited a surprising improvement in in vitro intrinsic clearance in microsomes (Assay 3) when compared with comparator compound X.

TABLE 1

| Assay 3 | Microsomal Cl (ml/min/g) | | | |
| --- | --- | --- | --- | --- |
|  | Rat | Dog | Cynomolgus monkey | Human |
| Comparator X | + | + | ++++ | ++ |
| Example 1 | + | + | + | + |
| Example 2 | + | + | ++, +++ | +, + |
| Example 3 | + | + | + | + |
| Example 4 | +, + | +, + | +++++, +++++ | ++, + |
| Example 5 | + | + | +++ | + |
| Example 6 | + | + | +++ | + |

Key to Table 1
+ corresponds to 1-8 ml/min/mg
++ corresponds to 9-15 ml/min/mg
+++ corresponds to 16-20 ml/min/mg
++++ corresponds to 21-30 ml/min/mg
+++++ corresponds to >31 ml/min/mg

The invention claimed is:
1. (3R,6R)-3-(2,3-dihydro-1H-inden-2-yl)-1-[(1R)-1-(2,6-dimethyl-3-pyridinyl)-2-(4-morpholinyl)-2-oxoethyl]-6-

[(1S)-1-methylpropyl]-2,5-piperazinedione or a pharmaceutically acceptable salt thereof wherein said pharmaceutically acceptable salt is an acid addition salt where the acid is selected from hydrochloric, hydrobromic, nitric, phosphoric, sulphuric, methanesulphonic, ethanesulphonic, benzenesulphonic, p-toluenesulphonic, citric, tartaric, lactic, pyruyic, acetic, succinic, fumaric and maleic acid.

2. A pharmaceutical composition comprising a compound according to claim 1 and a pharmaceutically acceptable carrier.

3. A method of treating premature ejaculation which comprises administering to a human in need thereof a compound according to claim 1.

4. A method of treating pre-term labour which comprises administering to a human in need thereof a compound according to claim 1.

* * * * *